(12) United States Patent
Kardos et al.

(10) Patent No.: US 9,212,125 B2
(45) Date of Patent: Dec. 15, 2015

(54) PROCESS FOR THE PREPARATION OF TRAVOPROST

(71) Applicant: CHINOIN GYÓGYSZER ÉS VEGYÉSZETI TERMÉKEK GYÁRA ZRT., Budapest (HU)

(72) Inventors: Zsuzsanna Kardos, Budapest (HU); Tibor Kiss, Budapest (HU); István Lászlofi, Budapest (HU); Irén Hortobágyi, Budapest (HU); Zoltán Bischof, Budapest (HU); Ádám Bódis, Budapest (HU); Gábor Havasi, Budapest (HU)

(73) Assignee: CHINOIN GYÓGYSZER ÉS VEGYÉSZETI TERMÉKEK GYÁRA ZRT., Budapest (HU)

( * ) Notice: Subject to any disclaimer, the term of this patent is extended or adjusted under 35 U.S.C. 154(b) by 0 days.

(21) Appl. No.: 14/367,317

(22) PCT Filed: Dec. 10, 2012

(86) PCT No.: PCT/HU2012/000132
§ 371 (c)(1),
(2) Date: Jun. 20, 2014

(87) PCT Pub. No.: WO2013/093528
PCT Pub. Date: Jun. 27, 2013

(65) Prior Publication Data
US 2014/0343299 A1    Nov. 20, 2014

(30) Foreign Application Priority Data
Dec. 21, 2011   (HU) .................................... 1100701

(51) Int. Cl.
| | | |
|---|---|---|
| *C07D 407/00* | (2006.01) | |
| *C07C 67/333* | (2006.01) | |
| *C07D 307/935* | (2006.01) | |
| *C07C 405/00* | (2006.01) | |
| *C07D 307/937* | (2006.01) | |

(52) U.S. Cl.
CPC ............. *C07C 67/333* (2013.01); *C07C 405/00* (2013.01); *C07D 307/935* (2013.01); *C07D 307/937* (2013.01); *C07C 2101/08* (2013.01)

(58) Field of Classification Search
CPC .................................................... C07C 405/00
USPC ........................................................ 549/312
See application file for complete search history.

(56) References Cited

FOREIGN PATENT DOCUMENTS

| | | | |
|---|---|---|---|
| CZ | 239696 B1 | 1/1986 | |
| EP | 2 143 712 A1 | 1/2010 | |
| WO | WO 2011/046569 A1 | 4/2011 | |

OTHER PUBLICATIONS

Written Opinion of the International Searching Authority, issued in PCT/HU2012/000132, dated Mar. 20, 2013 (Forms PCT/ISA/237 and PCT/IB/373).
Aswathanarayanappa et al., "Diastereoselective Reduction of the Enone Intermediate of Travoprost", Organic Process Research & Development, American Chemical Society, 15(5), Aug. 15, 2011, pp. 1085-1087.
International Search Report, issued in PCT/HU2012/000132, dated Mar. 20, 2013.
Search Report issued in Hungarian priority application P1100701, dated Jun. 15, 2012.
Written Opinion of the International Searching Authority, issued in PCT/HU2012/000132, dated Mar. 20, 2013.

*Primary Examiner* — Nizal Chandrakumar
(74) *Attorney, Agent, or Firm* — Birch, Stewart, Kolasch & Birch, LLP

(57) ABSTRACT

The invention relates to a process for the preparation of travoprost of formula (I), comprising that, the compound of formula (II), is stereoselectively reduced, the resulting compound of formula (III), is if desired crystallized, the lactone group of the compound of formula (III) is reduced, the p-phenyl-benzoyl protecting group of the thus obtained compound of formula (IV), is removed, the resulting triol of formula (V), is, if desired after crystallization, transformed by Wittig reaction into the acid of formula (VI), which is then esterified.

-continued
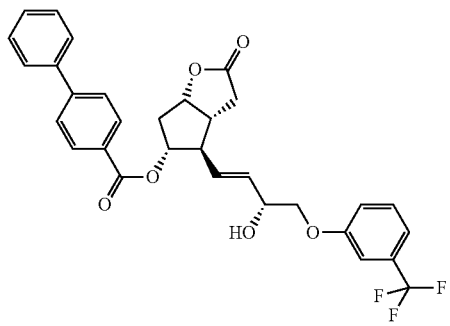
(III)
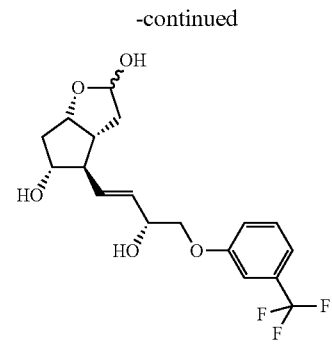
(V)
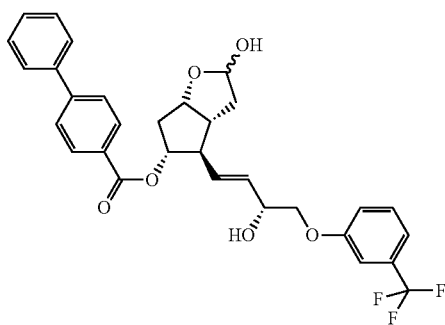
(IV)
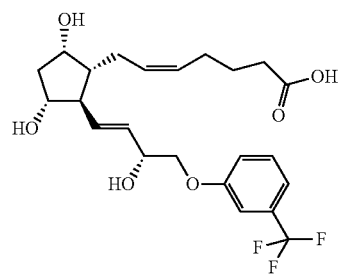
(VI)
24 Claims, 4 Drawing Sheets

Travoprost 1. intermediate IR spectrum:

Travoprost 2. intermediate IR spectrum:

Travoprost 3. intermediate IR spectrum:

Travoprost 4. intermediate IR spectrum:

Travoprost 5. intermediate IR spectrum:

Travoprost IR spectrum:

PROCESS FOR THE PREPARATION OF TRAVOPROST

The subject of our invention is a novel process for the preparation of travoprost. Travoprost of formula (I)

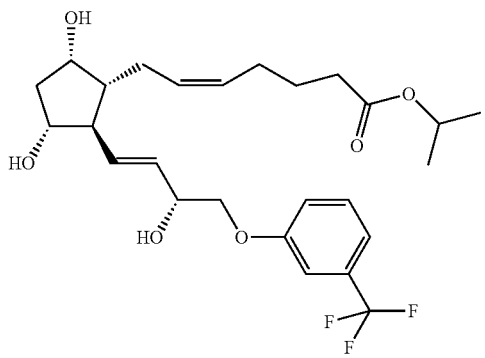 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

is a known prostaglandin derivative used for the treatment of glaucoma and high eye pressure (U.S. Pat. No. 5,510,383).

Processes for the preparation of travoprost are disclosed for example in EP 2143712, WO 2011/046569, WO 2011/055377.

Figure 1:
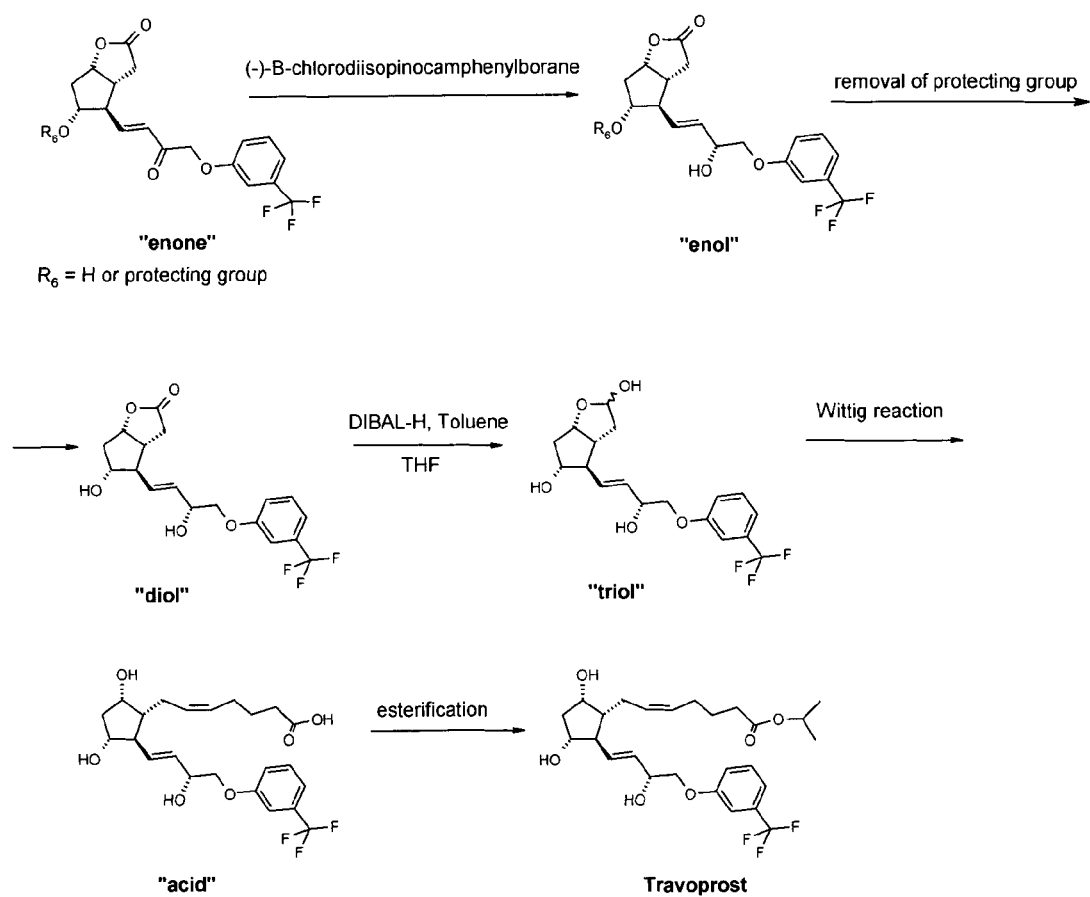
FIG. 1 illustrates the process according to EP 2143712.

The process according to EP 2143 712 is shown on FIG. 1.

Stereoselectivity of the enone→enol reduction is 88.7% (Example 10.).

According to the process disclosed in WO 2011/046569 the 15-epi impurity is removed by protection of the OH-groups of the diol with tert-butyl-dimethylsilyl group (TBDMS) and crystallization of the thus obtained protected diol.

In the process according to WO 2011/055377 the enone→enol transformation is carried out with N,N-diethylaniline-borane complex as reducing agent, in the presence of Corey catalyst (CBS-oxazaborolidine). The product is purified by preparative HPLC.

The overall yield is 7%.

We aimed to work out a process with higher stereoselectivity and better yield.

The subject of our invention is the preparation of travoprost of formula (I)

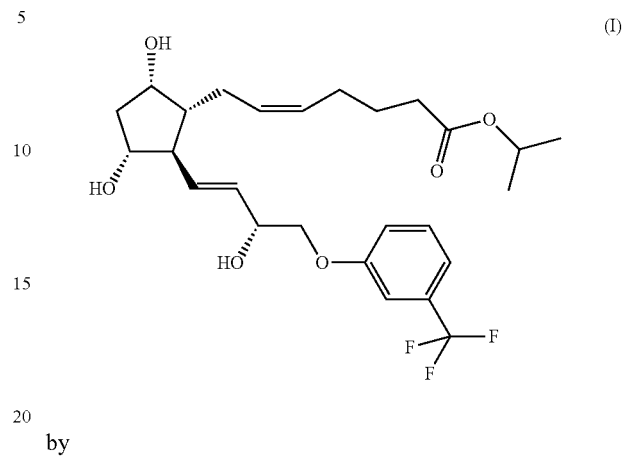

by stereoselective reduction of the compound of formula (II),

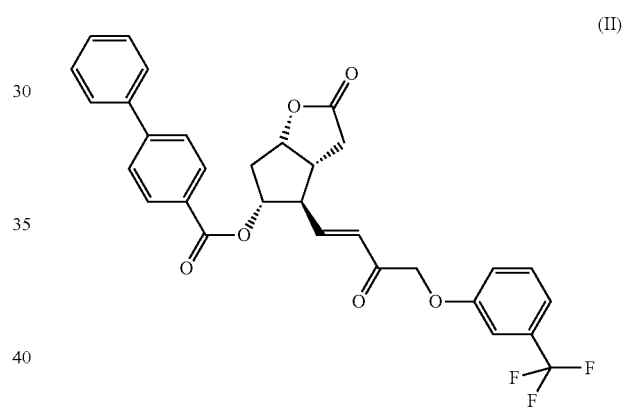

reduction of the lactone group of the resulting compound of formula (III),

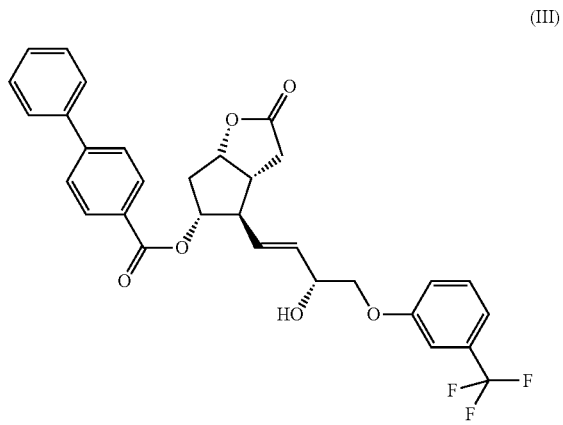

removal of the p-phenylbenzoyl protecting group of the thus obtained compound of formula (IV),

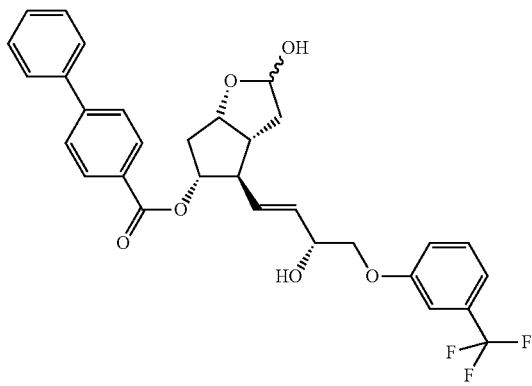

(IV)

transformation of the resulting triol of formula (V) by Wittig reaction

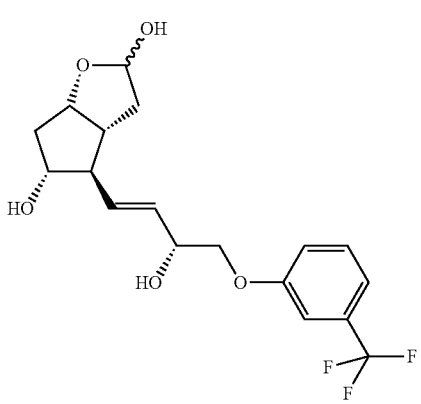

(V)

into the acid of formula (VI)

which is

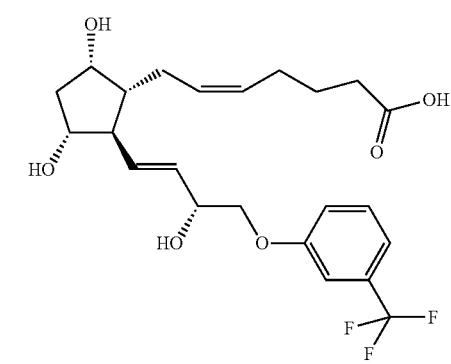

(VI)

then esterified.

The starting compound of formula (II) can be prepared for example by oxidation of the PPB-Corey-lactone of formula (XII)

into the

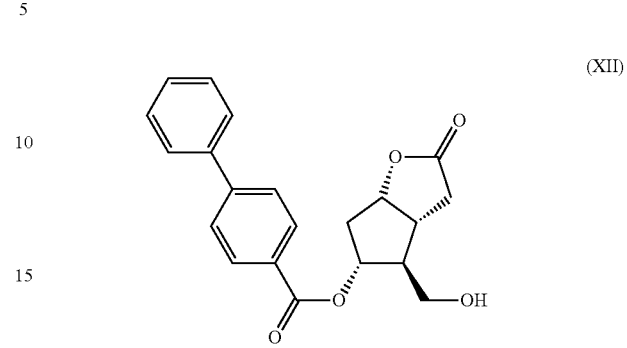

(XII)

aldehyde, which is then transformed with the phosphonate of formula (XIII)

(XIII)

in HWE reaction, in water free medium, in the presence of solid potassium hydroxide into the compound of formula (II).

According to one embodiment of the process based on the invention, the PPB-Corey-lactone is oxidized under Pfitzner-Moffatt reaction conditions into the aldehyde (Pfitzner, K. E., Moffatt J. G.; J. Am. Chem. Soc. 1963, 85, 3027), then the lower chain is built up with the help of Horner-Wadsworth-Emmons (HWE) reaction (Wadsworth, W.; Org. React., 1977, 25, 73)—by use of the appropriate phosphonate—under water-free conditions, in the presence of solid potassium hydroxide. For the deprotonation of the phosphonate—instead of using the widely described sodium hydride, potassium tert-butylate, lithium carbonate, DBU, lithium- or magnesium halogenides, triethylamine, potassium hexamethyl disilazide (KHMDS) or crown ether bases—we applied solid potassium hydroxide which is economical and can be safely used in industrial scale.

The HWE reaction is carried out in an aprotic organic solvent in a temperature range of 40-(−50)° C., preferably at (−10)° C., by using as solvent an aromatic hydrocarbon, such as toluene or an ether, like tetrahydrofuran, methyltetrahydrofuran, cyclopentyl methyl ether, dimethoxyethane, tert-butyl methyl ether, diisopropyl ether, diethyl ether or their mixtures. According to another embodiment of the invention, the selective reduction of the compound of formula (II) is accomplished with a borane-type reducing agent.

As the borane-type reducing agent borane-dimethyl sulfide, (−)-B-chlorodiisopinocampheylborane (DIP-Cl), catecholborane, especially catecholborane may be applied. According to a further embodiment of the process the reduction of the compound of formula (II) is carried out in the presence of a chiral catalyst. As chiral catalyst CBS-oxazaborolidine can be used. The reaction is carried out in the presence of an organic solvent, at a temperature between (10° C.) and (−80° C.), preferably between (−10° C.) and (−20° C.). As for solvent toluene, hexane, heptane, pentane, tetrahydrofuran, methyltetrahydrofuran, cyclopentyl methyl ether, dimethoxyethane, tert-butyl methyl ether, diisopropyl ether, diethyl ether or their mixtures may be applied, among others toluene-tetrahydrofuran mixtures are used.

The resulting compound of formula (III) is purified by crystallization, while the amount of the undesired isomer is lowered in a significant manner. The crystalline form of the compound of formula (III) has not been known before, it is a novel form. Crystallization is carried out in polar or apolar solvents or in the mixture of them.

In an embodiment of the process according to the invention the crystallization is performed between (−20)-70° C., in such a way that the material is dissolved in alcohol at reflux temperature and crystallized by cooling gradually. The crystals are then filtered off, washed and dried.

Reduction of the compound of formula (III) may be carried out with diisobutyl-aluminum hydride (DIBAL-H). As for solvent, inert aprotic solvents such as THF, toluene, hexane, and heptane may be applied. The reaction is performed at a temperature between (−80° C.) and (−50° C.), especially between (−80° C.) and (−70° C.).

The product of the DIBAL-H reduction, the intermediate of formula (IV), is a novel compound.

The PPB-protecting group may be removed in a known way by methanolysis, under basic conditions, especially in the presence of potassium carbonate.

In a further embodiment of the process, the resulting intermediate of formula (V) is purified by crystallization, while the amount of the undesired isomer is decreased under a strickt limit value. The crystalline form of the compound of formula (V) has not been described before, it is a novel form. Crystallization is carried out in the mixture of polar and apolar solvents. As for the mixture of polar and apolar solvents, an ethyl acetate-hexane mixture may be used. Transformation of the compound of formula (V) into the compound of formula (VI) is accomplished by Wittig reaction, while esterification of the compound of formula (VI) is carried out with isopropyl iodide.

In the esterification reaction cyclic tertiary amides, such as N-methylpyrrolidone and/or 1,3-dimethylimidazolidinone are used as solvents. The esterification is performed at a temperature between 20-90° C., especially between 40-50° C.

A further subject of the invention is the novel compound of formula (IV)

(IV)

and its use for the preparation of Travoprost.

Furthermore, the subject of the invention is the crystalline compound of formula (III),

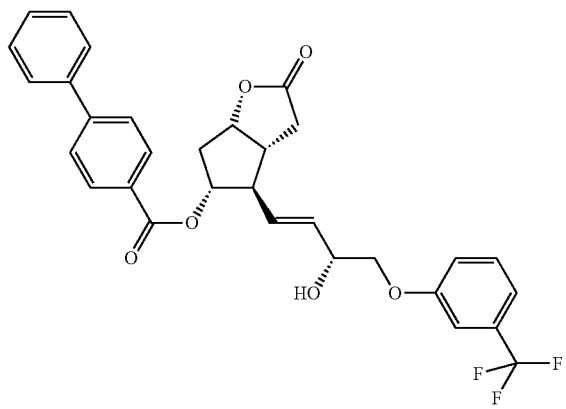

(III)

having the melting point of 129.5-134.5° C., and its use for the preparation of Travoprost.

Furthermore, the subject of the invention is the crystalline compound of formula (V), (V)

having the melting point of 85.4-86.6° C., and its use for the preparation of Travoprost.

One embodiment of the full synthesis of Travoprost according to the invention is demonstrated on Scheme 1 below:

Scheme 1

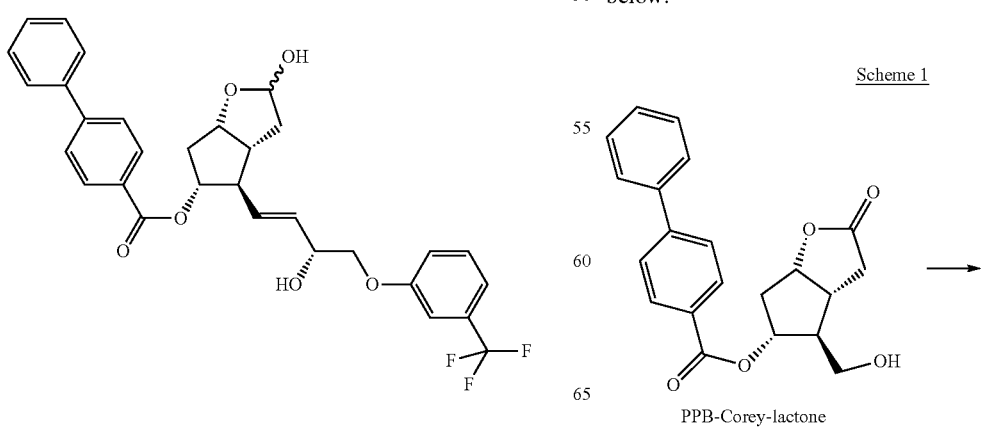

PPB-Corey-lactone

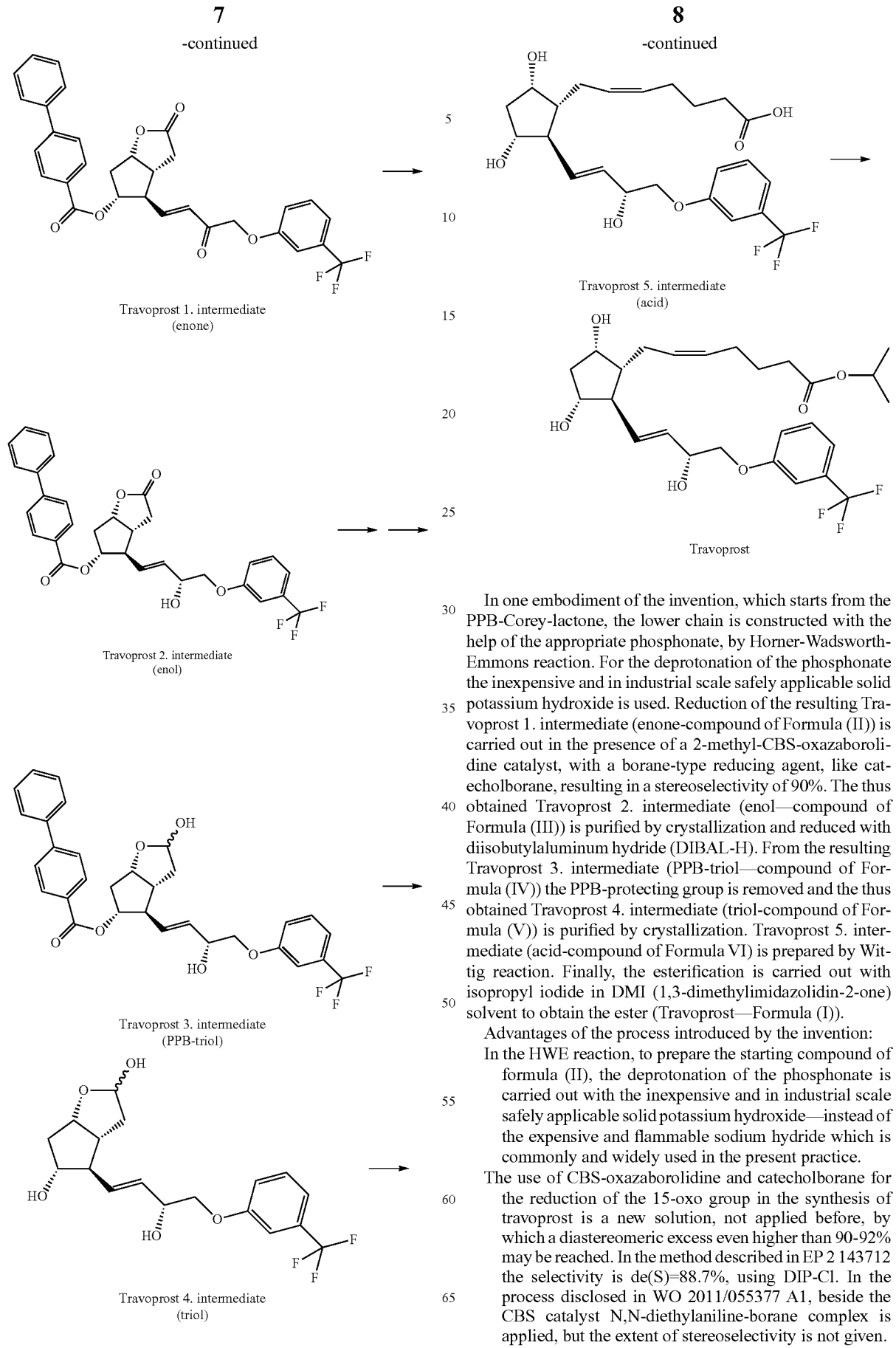

In one embodiment of the invention, which starts from the PPB-Corey-lactone, the lower chain is constructed with the help of the appropriate phosphonate, by Horner-Wadsworth-Emmons reaction. For the deprotonation of the phosphonate the inexpensive and in industrial scale safely applicable solid potassium hydroxide is used. Reduction of the resulting Travoprost 1. intermediate (enone-compound of Formula (II)) is carried out in the presence of a 2-methyl-CBS-oxazaborolidine catalyst, with a borane-type reducing agent, like catecholborane, resulting in a stereoselectivity of 90%. The thus obtained Travoprost 2. intermediate (enol—compound of Formula (III)) is purified by crystallization and reduced with diisobutylaluminum hydride (DIBAL-H). From the resulting Travoprost 3. intermediate (PPB-triol—compound of Formula (IV)) the PPB-protecting group is removed and the thus obtained Travoprost 4. intermediate (triol-compound of Formula (V)) is purified by crystallization. Travoprost 5. intermediate (acid-compound of Formula VI) is prepared by Wittig reaction. Finally, the esterification is carried out with isopropyl iodide in DMI (1,3-dimethylimidazolidin-2-one) solvent to obtain the ester (Travoprost—Formula (I)).

Advantages of the process introduced by the invention:
In the HWE reaction, to prepare the starting compound of formula (II), the deprotonation of the phosphonate is carried out with the inexpensive and in industrial scale safely applicable solid potassium hydroxide—instead of the expensive and flammable sodium hydride which is commonly and widely used in the present practice.
The use of CBS-oxazaborolidine and catecholborane for the reduction of the 15-oxo group in the synthesis of travoprost is a new solution, not applied before, by which a diastereomeric excess even higher than 90-92% may be reached. In the method described in EP 2 143712 the selectivity is de(S)=88.7%, using DIP-Cl. In the process disclosed in WO 2011/055377 A1, beside the CBS catalyst N,N-diethylaniline-borane complex is applied, but the extent of stereoselectivity is not given.

The purification strategy is fully novel, since removal of the 15-epi-impurity is accomplished by crystallization, without chromatography, in a high yield, contrary to the MPLC (medium pressure chromatography purification method) (WO 2011/046569 A1) or preparative HPLC (WO 2011/055377 A1) methods known in the literature.

The crystalline form of the compound of formula (III) and that of the compound of formula (V) have not been described in the literature before. In the present process the crystalline form is also utilized for the purification of the intermediates and removal of the undesired isomer.

In the esterification step, as a novel solvent, 1,3-dimethylimidazolidinone (DMI) is used, which is not strongly toxic, in contrast to the generally used dimethylformamide (EP 2 143 712 A1, WO 2011/046569 A1). DMI is a solvent used in the beauty industry. As a further advantage, the formyl-impurities which generate from the widely used dimethylformamide solvent, are not formed from DMI. The esterification reaction can be carried out with very high conversion, without forming new impurities (~100%).

The overall yield of the new process is very high, 16%, which is more than double of the yield described in WO 2011/055377 A1 (7%).

Further details of the invention are included, but not limited to the examples below.

EXAMPLES

1. Construction of the Lower Chain (Oxidation and HWE Reaction)

Preparation of the [1,1'-Biphenyl]-4-carboxylic acid, (3aR, 4R,5R,6aS)-hexahydro-2-oxo-4-[(1E)-3-oxo-4-[3-(trifluoromethyl)phenoxy]-1-buten-1-yl]-2H-cyclopenta[b]furan-5-yl ester /compound of formula (II)/

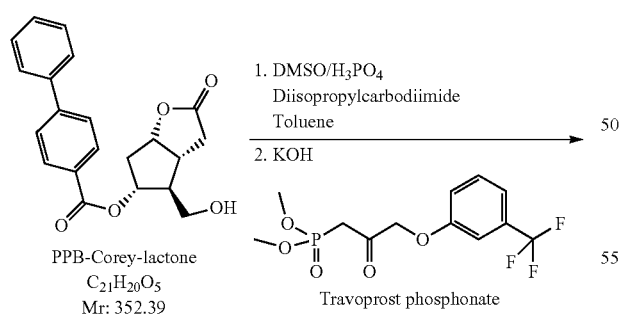

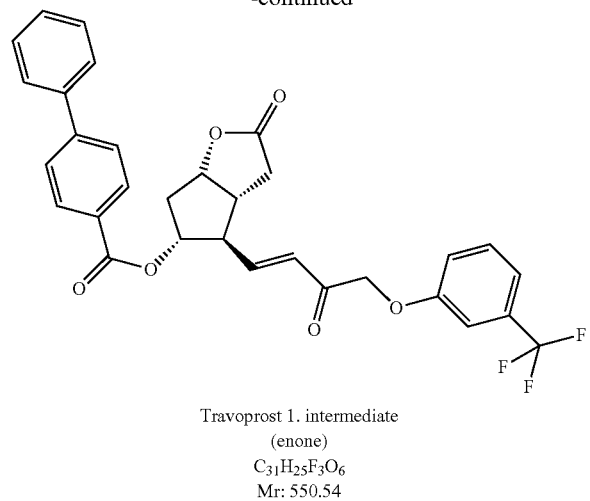

Travoprost 1. intermediate
(enone)
$C_{31}H_{25}F_3O_6$
Mr: 550.54

1069 g of PPB-Corey-lactone is suspended in an inert atmosphere in 11.1 L of water-free toluene. To this suspension are added 1.4 L of diisopropylcarbodiimide and then 0.855 L of dimethyl sulfoxide in phosphoric acid. The reaction mixture is heated to 50° C. and a further 0.34 L of dimethyl sulfoxide in phosphoric acid is added in portions. After the accomplishment of the oxidation reaction, the mixture is cooled to −10° C. and while that temperature is maintained, 316 g of potassium hydroxide followed by 1.45 kg of Travoprost phosphonate in toluene solution are added. When the HWE reaction has completed, the reaction mixture is poured onto 1 M hydrochloric acid solution and the mixture is stirred. The precipitated crystals are filtered off and washed. The phases of the filtrate are separated, the organic phase is washed with 1M sodium hydrogen carbonate solution and then with diluted hydrochloric acid solution. The organic phase is evaporated and purified by chromatography on a silica gel column (eluent: toluene-ethyl acetate mixture). The main fraction is evaporated and crystallized from ethyl acetate-hexane mixture.

Yield: 915 g, 55%.

Melting point: 112.5-114.5° C.

Figure 2:
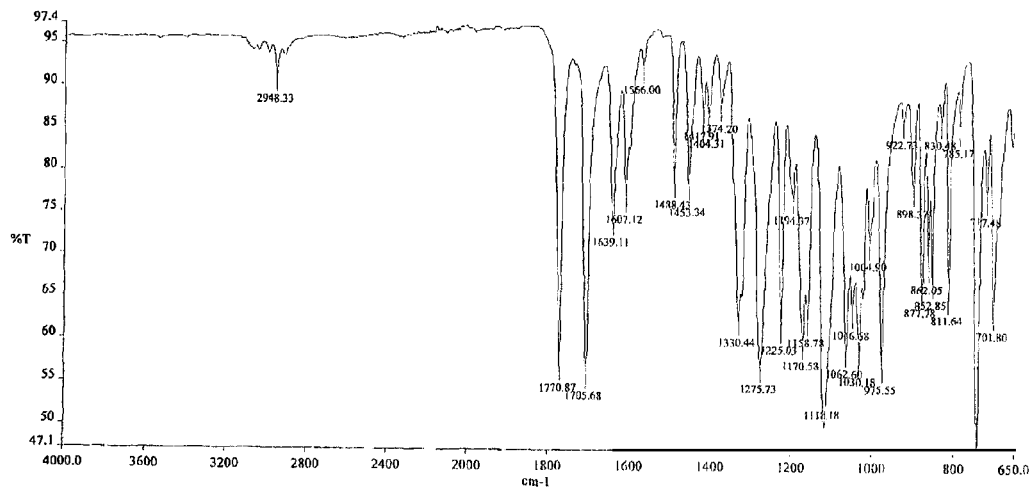
FIG. 2 is the IR spectrum of the Travopost 1. intermediate.

IR spectrum of Travoprost 1. intermediate is shown on FIG. 2.

Travoprost 1. intermediate $^1H$, $^{13}C$ and $^{19}F$ NMR data:

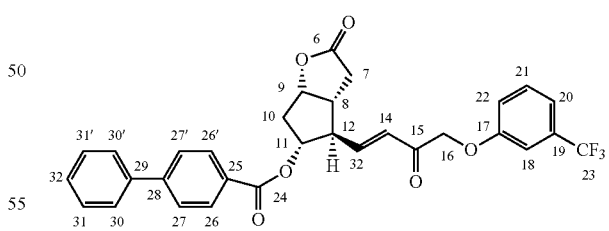

Travoprost 1. intermediate (enone—Formula (II)):

| Numbering | $^{13}C/^{19}F$ (ppm) | $^1H$ (ppm) | Number of $^1H$ | Multiplicity | Coupling constant (Hz) (+/− 0.2 Hz) |
|---|---|---|---|---|---|
| 6 | 176.56 | — | — | | |
| 7 | 34.46 | β: 2.96* | 1 | m (dd) | $J_{gem} = 17.3; J_{7\beta,8} = 10.2$ |
| | | α: 2.55 | 1 | d | |
| 8 | 42.17 | 3.00* | 1 | m (dddd) | |

-continued

| Numbering | $^{13}C/^{19}F$ (ppm) | $^1H$ (ppm) | Number of $^1H$ | Multiplicity | Coupling constant (Hz) (+/− 0.2 Hz) |
|---|---|---|---|---|---|
| 9 | 83.32 | 5.13 | 1 | td | $J_{8,9} = J_{9,10\beta} = 6.4$; $J_{9,10\alpha} = 1.3$ |
| 10 | 37.50 | β: 2.63 | 1 | dt | $J_{gem} = 15.2$; $J_{10\beta,11} = 6.4$; |
|  |  | α: 2.14 | 1 | dd | $J_{10\alpha,11} = 3.6$ |
| 11 | 78.95 | 5.35 | 1 | dt | $J_{11,12} = 5.6$ |
| 12 | 53.66 | 3.10 | 1 | m (ddd) | $J_{8,12} = 5.0$ |
| 13 | 146.19 | 6.99 | 1 | dd | $J_{13,14} = 16.0$; $J_{12,13} = 8.1$ |
| 14 | 127.24 | 6.44 | 1 | d |  |
| 15 | 194.08 | — | — | — |  |
| 16 | 71.12 | 5.17 | 2 | s |  |
| 17 | 158.14 | — | — | — |  |
| 18 | 111.16 (q) | 7.22** | 1 | broad | $^3J_{C-18,F} = 3.8$; $J_{18,20} = 1.5$; $J_{18,22} = 2.5$ |
| 19 | 130.24 (q) | — | — | — | $^2J_{C-19,F} = 31.7$ |
| 20 | 117.50 (q) | 7.285 | 1 | m (d) | $^3J_{C-20,F} = 3.8$; $J_{20,21} = 7.8$; $J_{20,22} = 0.8$; |
| 21 | 130.63 | 7.495*** | 1 | m (dd) | $J_{21,22} = 8.2$ |
| 22 | 118.75 | 7.20** | 1 | m (dd) |  |
| 23 | 123.95 (q) | — | — | — | $^1J_{C-23,F} = 272.5$ |
| 23-F | −61.10 (s, 3) | — | — | — |  |
| 24 | 164.94 | — | — | — |  |
| 25 | 128.16 | — | — | — |  |
| 26, 26' | 129.95 | 8.015 | 2 | m | $J_{26,27} = 8.5$; |
| 27, 27' | 126.87 | 7.81 | 2 | m |  |
| 28 | 144.93 | — | — | — |  |
| 29 | 138.77 | — | — | — |  |
| 30, 30' | 127.01 | 7.74 | 2 | m (dd) | $J_{30,31} = 7.4$ |
| 31, 31' | 129.10 | 7.51*** | 2 | m (t) | $J_{31,32} = 7.4$ |
| 32 | 128.46 | 7.43 | 1 | m (tt) | $J_{30,32} \sim 1.6$ |

*, , *Overlapping $^1H$ NMR signals 2. 15-oxo-reduction (Stereoselective Reduction)

Preparation of [1,1'-Biphenyl]-4-carboxylic acid, (3aR,4R, 5R,6aS)-hexahydro-4-[(1E,3R)-3-hydroxy-4-[3-(trifluoromethyl)phenoxy]-1-buten-1-yl]-2-oxo-2H-cyclopenta [b]furan-5-yl ester /compound of formula (III)/

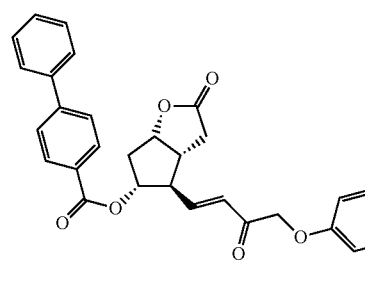

Travoprost 1. intermediate
(enone)
$C_{31}H_{25}F_3O_6$
Mr: 550.54 catecholborane
R-(+)-2-methyl-CBS-oxazaborolidine
THF
→

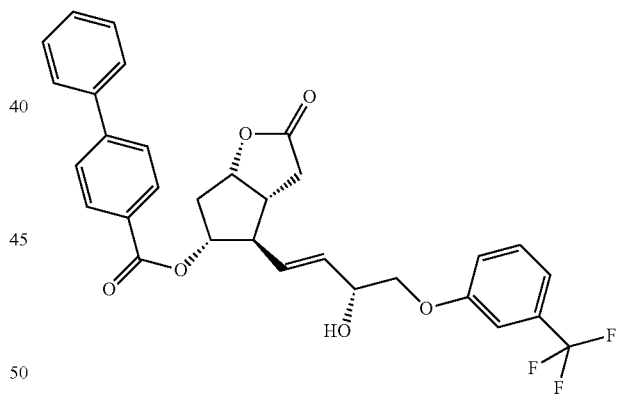

Travoprost 2. intermediate
(enol)
$C_{31}H_{27}F_3O_6$
Mr: 552.55

279 ml of catecholborane is dissolved in 4.6 L of tetrahydrofuran (THF) and the 1M toluene solution of 549 ml of R-(+)-2-methyl-CBS-oxazaborolidine is added to it. The mixture is cooled to −10° C. and while that temperature is maintained, the solution of 915 g of Travoprost 1. intermediate (enone—compound of Formula (II)) in 6.9 L of THF is added. When the reaction has completed, the mixture is decomposed by stirring with 13 L of 1 M NaHSO$_4$ solution. Ethyl acetate is then added and the phases are separated. The organic phase is washed with NaOH solution and then with hydrochloric acid solution. The organic phase is dried over sodium sulfate, filtered, evaporated and crystallized first from hexane: acetone mixture, then from methanol for removing the undesired isomer de(S)$_{92}$%->de(S)98%. (de means: diastereomeric excess)

Yield: 701 g, 55% de(S): 98%

M.p.: 129.5-134.5° C.

Figure 3:
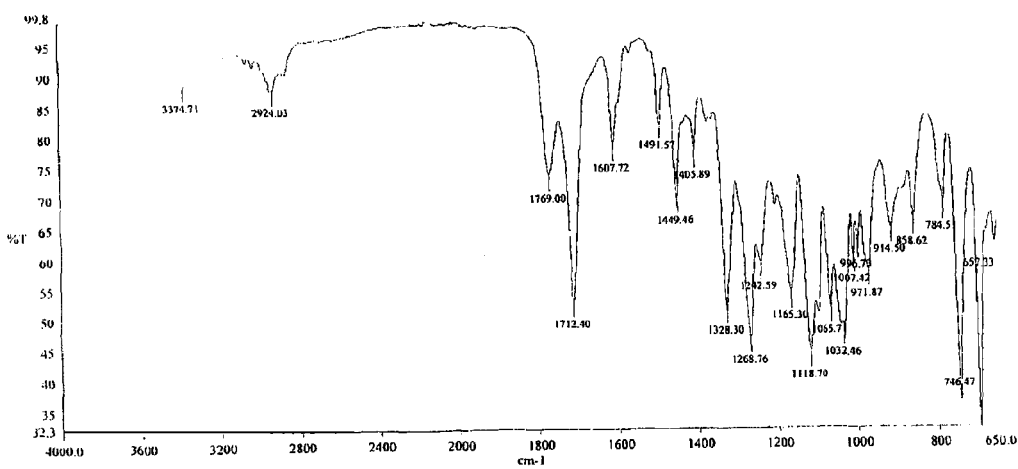
FIG. 3 is the IR spectrum of the Travopost 2. intermediate.

IR spectrum of Travoprost 2. intermediate is shown on FIG. 3.
Travoprost 2. intermediate $^1$H, $^{13}$C and $^{19}$F NMR data:

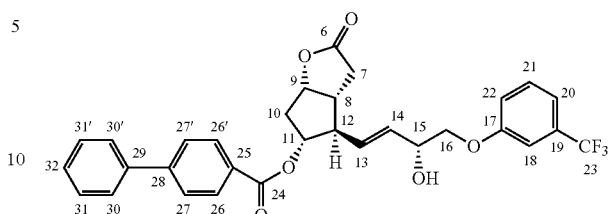

| Numbering | $^{13}$C/$^{19}$F (ppm) | $^1$H (ppm) | Number of $^1$H | Multiplicity | Coupling constant (Hz) (+/- 0.2 Hz) |
|---|---|---|---|---|---|
| 6 | 176.76 | — | — | — | |
| 7 | 34.53 | β: 2.93 | 1 | dd | $J_{gem} = 17.8; J_{7\beta,8} = 10.0$ |
|   |       | α: 2.46 | 1 | dd | $J_{7\alpha,8} = 0.9$ |
| 8 | 42.14 | 2.85* | 1 | m (dddd) | |
| 9 | 83.28 | 5.09 | 1 | td | $J_{8,9} = J_{9,10\beta} = 6.5;$ |
|   |       |      |   |    | $J_{9,10\alpha} = 1.4$ |
| 10 | 37.20 | β: 2.55 | 1 | dt | $J_{gem} = 15.2; J_{10\beta,11} = 6.4;$ |
|    |       | α: 2.05 | 1 | m (dd) | $J_{10\alpha,11} = 4.6$ |
| 11 | 79.58 | 5.20 | 1 | m (ddd/dt) | $J_{11,12} \sim 5.5$ |
| 12 | 53.49 | 2.83* | 1 | m (ddd) | |
| 13 | 129.87$ | 5.76** | 1 | m | |
| 14 | 132.18 | 5.76** | 1 | m | |
| 15 | 68.83 | 4.34 | 1 | m (broad) | |
| 15-OH | | 5.26 | 1 | d | $J_{15, OH} = 4.9$ |
| 16 | 72.18 | a: 3.95 | 1 | dd | $J_{gem} = 9.8; J_{15,16a} = 4.6;$ |
|    |       | b: 3.90 | 1 | dd | $J_{15,16b} = 6.7$ |
| 17 | 158.88 | — | — | — | |
| 18 | 111.08 (q) | 7.195*** | 1 | m | $^3J_{C-18,F} = 3.7$ |
| 19 | 130.25 (q) | — | — | — | $^2J_{C-19,F} = 31.5$ |
| 20 | 117.04 (q) | 7.25 | 1 | d | $^3J_{C-20,F} = 3.7;$ |
|    |            |      |   |   | $J_{20,21} = 7.7; J_{18,20} = 1.4;$ |
|    |            |      |   |   | $J_{20,22} = 1.0$ |
| 21 | 130.63 | 7.47# | 1 | m (t/dd) | $J_{21,22} = 8.2$ |
| 22 | 118.80 | 7.20*** | 1 | m | $J_{18,22} = 2.5;$ |
| 23 | 123.98 (q) | — | — | — | $^1J_{C-23,F} = 272.4$ |
| 23-F | −61.16 (s, 3) | — | — | — | |
| 24 | 165.02 | — | — | — | |
| 25 | 128.33 | — | — | — | |
| 26, 26' | 129.87$ | 7.99 | 2 | d | $J_{26,27} = 8.4$ |
| 27, 27' | 126.80 | 7.77 | 2 | d | |
| 28 | 144.81 | — | — | — | |
| 29 | 138.77 | — | — | — | |
| 30, 30' | 126.97 | 7.72 | 2 | d | $J_{30,31} = 7.4$ |
| 31, 31' | 129.07 | 7.50# | 2 | m (t) | $J_{31,32} = 7.4$ |
| 32 | 128.42 | 7.43# | 1 | m (tt) | |

*, , *, #, ##: Overlapping $^1$H NMR signals.

$: Overlapping $^{13}$C NMR signals.

3. Lactone reduction (Preparation of the Lactol)

Preparation of [1,1'-Biphenyl]-4-carboxylic acid, (3 aR,4R, 5R,6aS)-hexahydro-4-[(1E,3R)-3-hydroxy-4-[3-(trifluoromethyl)phenoxy]-1-buten-1-yl]-2-hydroxy-cyclopenta[b]furan-5-yl ester /compound of formula (IV)/

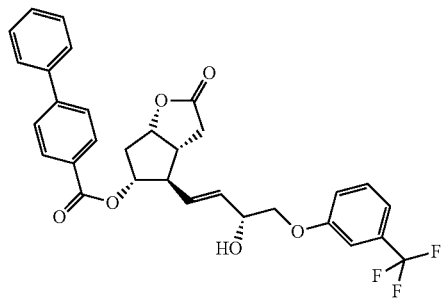

Travoprost 2. intermediate
(enol)
$C_{31}H_{27}F_3O_6$
Mr: 552.55

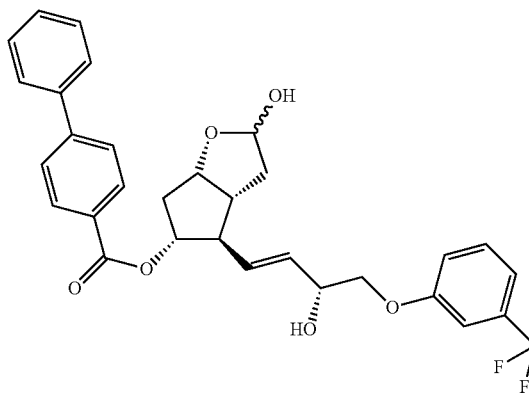

Travoprost 3. intermediate
(PPB-triol)
$C_{31}H_{29}F_3O_6$
Mr: 554.57

A multi-neck flask is charged under nitrogen atmosphere with 701 g of enol which is then dissolved in 6.8 L of room temperature THF. The clear solution is cooled to −75° C. and in approximately 30 minutes the pre-cooled (−75° C.) 1 M hexane solution of 2921 ml diisobutylaluminum hydride (DIBAL-H) is added to it. The reaction mixture is stirred at −75° C. until the reaction is completed. After reaching the suitable conversion, the reaction mixture is poured onto the mixture of $NaHSO_4$ solution and ethyl acetate. The phases are separated, the aqueous phase is extracted with ethyl acetate, the united organic phase is washed with $NaHCO_3$ solution and with diluted hydrochloric acid solution, and then evaporated while adding triethylamine (TEA) to it. 639.5 g oil is obtained.

Yield: 639.5 g, 91%

Figure 4:
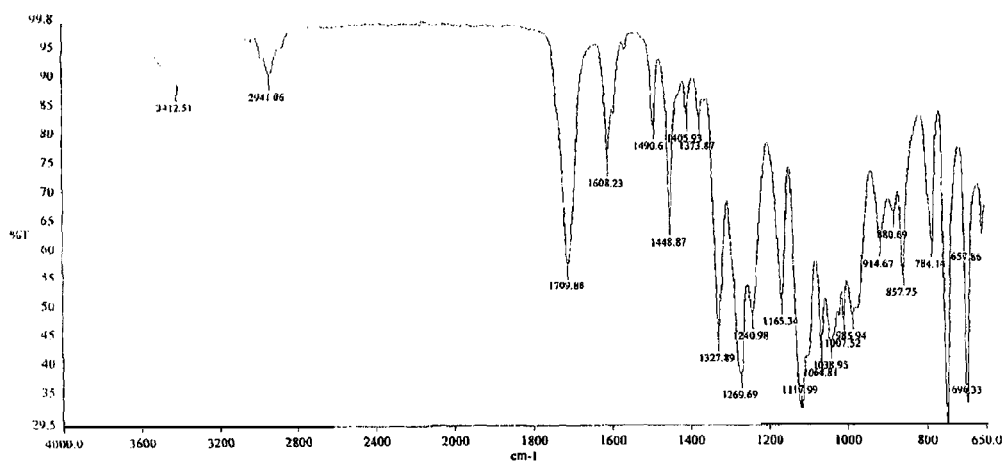
FIG. 4 is the IR spectrum of the Travopost 3. intermediate.

IR spectrum of Travoprost 3. intermediate is shown on FIG. 4.

Travoprost 3. intermediate $^1H$, $^{13}C$ and $^{19}F$ NMR data:

A)

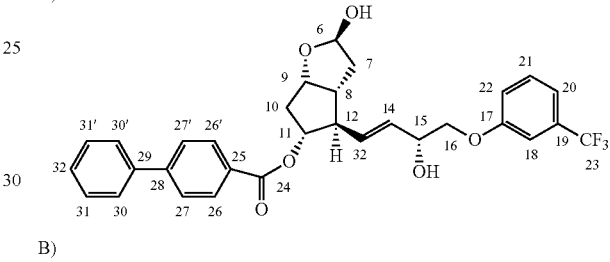

B)

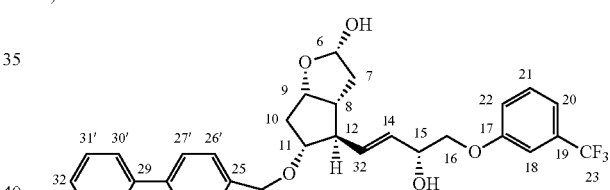

Travoprost 3. intermediate, diastereomer A

| Numbering | $^{13}C/^{19}F$ (ppm) | $^1H$ (ppm) | Number of $^1H$ | Multiplicity | Coupling constant (Hz) (+/−0.2 Hz) |
|---|---|---|---|---|---|
| 6 | 98.78 | 5.53 | 1 | td | $J_{6,OH}$ = 4.6; $J_{6,7}$ = 2.2 and 4.6 |
| 6-OH |  | 6.02 | 1 | d |  |
| 7 | 39.31$ | a: 1.93* | 1 | m |  |
|  |  | b: 1.89* | 1 | m |  |
| 8 | 45.28 | 2.565** | 1 | m |  |
| 9 | 79.43 | 4.565 | 1 | td | $J_{8,9}$ = 6.2; $J_{9,10}$ = 2.7 and 6.2 |
| 10 | 37.21 | β: 2.51 | 1 | m | $J_{gem}$~14.0 |
|  |  | α: 1.74*** | 1 | m (ddd) | $J_{10\alpha,11}$ = 6.9 |
| 11 | 79.72 | 5.08 | 1 | m (q/dt) | $J_{10\beta,11}$ = $J_{11,12}$ = 6.9 |
| 12 | 53.23 | 2.575** | 1 | m |  |
| 13 | 130.60 | 5.75+ | 1 | dd | $J_{13,14}$ = 15.6; $J_{12,13}$ = 6.5 |
| 14 | 131.71 | 5.70+ | 1 | dd | $J_{14,15}$ = 4.5 |
| 15 | 68.79 | 4.32++ | 1 | m (dddd) |  |
| 15-OH |  | 5.23+++ | 1 | m (d) | $J_{15,OH}$ = 5.0 |
| 16 | 72.23$$ | a: 3.91# | 1 | m (dd) | $J_{gem}$ = 9.7; $J_{15,16a}$ = 4.8; |
|  |  | b: 3.87# | 1 | m (dd) | $J_{15,16b}$ = 6.7 |
| 17 | 158.88$$ | — | — | — |  |
| 18 | 111.09 (q) | 7.16## | 1 | m | $^3J_{C-18,F}$ = 3.6; $J_{18,20}$~$J_{18,22}$~1.3 |

-continued

| Numbering | $^{13}C/^{19}F$ (ppm) | $^1$H (ppm) | Number of $^1$H | Multiplicity | Coupling constant (Hz) (+/−0.2 Hz) |
|---|---|---|---|---|---|
| 19 | 130.24$^{\$\$}$ (q) | — | — | — | $^2J_{C-19,F} = 31.7$ |
| 20 | 117.01$^{\$\$}$ (q) | 7.22$^{\#\#\#}$ | 1 | m | $^3J_{C-20,F} = 3.8; J_{20,21} = 7.8$ |
| 21 | 130.56 | 7.44$^{\&}$ | 1 | m (t/dd) | $J_{21,22} = 7.8$ |
| 22 | 118.73 | 7.15$^{\#\#}$ | 1 | m | |
| 23 | 123.97$^{\$\$}$ (q) | — | — | — | $^1J_{C-23,F} = 272.4$ |
| 23-F | −61.19 (s, 3) | — | — | — | |
| 24 | 165.16 | — | — | — | |
| 25 | 128.61 | — | — | — | |
| 26, 26' | 129.75$^{\$\$}$ | 7.985$^{\&\&}$ | 2 | d | $J_{26,27} = 8.4$ |
| 27, 27' | 126.90$^{\$\$}$ | 7.77 | 2 | d | |
| 28 | 144.71$^{\$\$}$ | — | — | — | |
| 29 | 138.84$^{\$\$}$ | — | — | — | |
| 30, 30' | 126.96$^{\$\$}$ | 7.70$^{\&\&\&}$ | 2 | m (d) | $J_{30,31} = 7.5$ |
| 31, 31' | 129.07$^{\$\$}$ | 7.50$^{€}$ | 2 | m (t/dd) | $J_{31,32} = 7.4$ |
| 32 | 128.40$^{\$\$}$ | 7.43$^{\&}$ | 1 | m (tt) | |

*, , *, +, ++, +++, #, ##, ###, &, &&, &&&, €Overlapping $^1$H NMR signals.
$^{\$}$Overlapping $^{13}$C NMR signals with the DMSO signal.
$^{\$\$}$Overlapping $^{13}$C NMR signals.

Travoprost 3. intermediate, diastereomer B

| Numbering | $^{13}C/^{19}F$ (ppm) | $^1$H (ppm) | Number of $^1$H | Multiplicity | Coupling constant (Hz) (+/−0.2 Hz) |
|---|---|---|---|---|---|
| 6 | 99.70 | 5.45 | 1 | m (td/ddd) | $J_{6,7} = 0.9$ and 4.5 |
| 6-OH | | 6.25 | 1 | d | $J_{6,OH} = 3.4$ |
| 7 | 37.51 | β: 1.99$^{€}$ | 1 | m | $J_{7,8β} = 5.7$ |
| | | α: 1.73*** | 1 | m | $J_{gem}\sim11.8; J_{6,7α} = 1.9$ |
| 8 | 44.64 | 2.41 | 1 | m (q/ddd) | $J_{8,12} = 10.1$ |
| 9 | 80.04 | 4.46 | 1 | td | $J_{8,9} = J_{9,10β} = 7.3; J_{9,10α} = 5.2$ |
| 10 | 39.45$^{\$}$ | β: 2.65 | 1 | dt | $J_{gem} = 13.0; J_{10β,11} = 7.3$ |
| | | α: 1.90* | 1 | m | |
| 11 | 78.11 | 5.00 | 1 | td | $J_{10α,11} = J_{11,12} = 9.8$ |
| 12 | 52.34 | 3.10 | 1 | td | $J_{12,13} = 7.1$ |
| 13 | 130.74 | | | | |
| 14 | 131.85 | | | | |
| 15 | 68.68 | | | | |
| 15-OH | | 5.21$^{+++}$ | 1 | m (d) | $J_{15,OH} = 5.1$ |
| 16 | 72.25$^{\$\$}$ | a: 3.88$^{\#}$ | 1 | m | $J_{gem} = 9.7$ |
| | | b: 3.84$^{\#}$ | 1 | m (dd) | $J_{15,16b} = 6.6$ |
| 17 | 158.86$^{\$\$}$ | — | — | — | |
| 19 | 130.22$^{\$\$}$ (q) | — | — | — | $^2J_{C-19,F} = 31.7$ |
| 20 | 116.97$^{\$\$}$ (q) | 7.205$^{\#\#\#}$ | 1 | m | $^3J_{C-20,F} = 3.8; J_{20,21} = 7.8$ |
| 21 | | 7.41$^{\&}$ | 1 | m (dd) | $J_{21,22} = 8.1$ |
| 22 | 118.64 | 7.11$^{\#\#}$ | 1 | m (dd) | 2.3; 0.8 |
| 23 | 123.95$^{\$\$}$ (q) | — | — | — | $^1J_{C-23,F} = 272.4$ |
| 23-F | −61.21 (s, 3$^{\%}$) | — | — | — | |
| 24 | 165.28 | — | — | — | |
| 25 | 128.57 | — | — | — | |
| 26, 26' | 129.76$^{\$\$}$ | 7.995$^{\&\&}$ | 2 | d | $J_{26,27} = 8.4$ |
| 27, 27' | 126.85$^{\$\$}$ | 7.73 | 2 | d | |
| 28 | 144.68$^{\$\$}$ | — | — | — | |
| 30, 30' | 126.94$^{\$\$}$ | 7.68$^{\&\&\&}$ | 2 | m (d) | $J_{30,31} = 7.5$ |
| 31, 31' | 129.065$^{\$\$}$ | | | | |

*, ***, +++, #, ##, ###, &, &&, &&&: Overlapping $^1$H NMR signals.
$^{\$}$Overlapping $^{13}$C NMR signals with the signal of DMSO.
$^{€}$Overlapping $^1$H NMR signals with the signal of ethyl acetate.
$^{\$\$}$Overlapping $^{13}$C NMR signals.
$^{\%}$The presence of the 3 fluoro atoms is shown by the $^{19}$F and $^{13}$C NMR spectra.

4. Removal of the Protecting Group (Preparation of the Triol)
4a.
Preparation of 2H-cyclopenta[b]furan-2,5-diol, hexahydro-4-[(1E,3R)-3-hydroxy-4-[3-(trifluoromethyl)phenoxy]-1-buten-1-yl]-, (3 aR,4R,5R,6aS)-
/Compound of formula (V)/

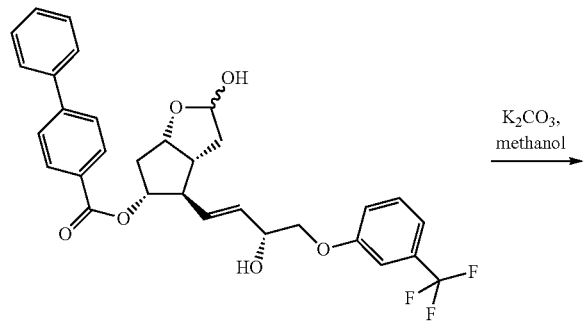

Travoprost 3. intermediate
(PPB-triol)
$C_{31}H_{29}F_3O_6$
Mr: 554.57

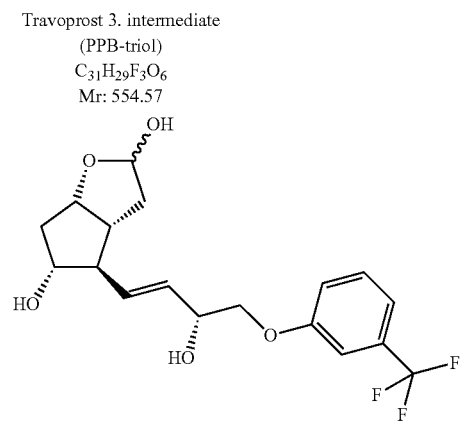

Travoprost 4. intermediate
(triol)
$C_{18}H_{21}F_3O_5$
Mr: 374.36

639.5 g of PPB-triol is dissolved in 6.4 L of methanol and the solution is heated to 40° C. 95 g of $K_2CO_3$ is added and the mixture is stirred at 40° C. until the reaction is completed. After reaching the suitable conversion, the reaction mixture is cooled to 2° C. and phosphoric acid solution is added in portions. The precipitated PPB-methyl ester crystals are filtered off and washed. The filtrate is concentrated, water and ethyl acetate are added and the phases are separated. The aqueous phase is extracted with ethyl acetate, dried over $Na_2SO_4$ and the solution is evaporated. The crude oil is crystallized from ethyl acetate:hexane mixture. The precipitated crystals are filtered off, washed with hexane:ethyl acetate mixture and dried.
Yield: 367 g, 85%
Melting point: 85.4-86.6° C.
4b.
Recrystallyzation of 2H-cyclopenta[b]furan-2,5-diol, hexahydro-4-[(1E,3R)-3-hydroxy-4-[3-(trifluoromethyl) phenoxy]-1-buten-1-yl]-, (3 aR,4R,5R,6aS)-
/Compound of formula (V)—the triol/

The precipitated crystals are solved in 10 folds ethyl-acetate, thereafter 10 folds n-hexane is added and the solution is mixed at room temperature. To the crystal-suspension obtained 20 folds n-hexane is added and mixed at room temperature. The precipitated crystals are filtered, washed with a mixture of hexane:ethyl-acetate and dried. With repetition of the above process at any time the amount of the undesired isomer may be lowered to any amount, also decreasing of the amount of the undesired isomer under the disregard limit (<0.05%) is possible.
Yield: 52-85% (depending of the number of recrystallizations)

Figure 5:
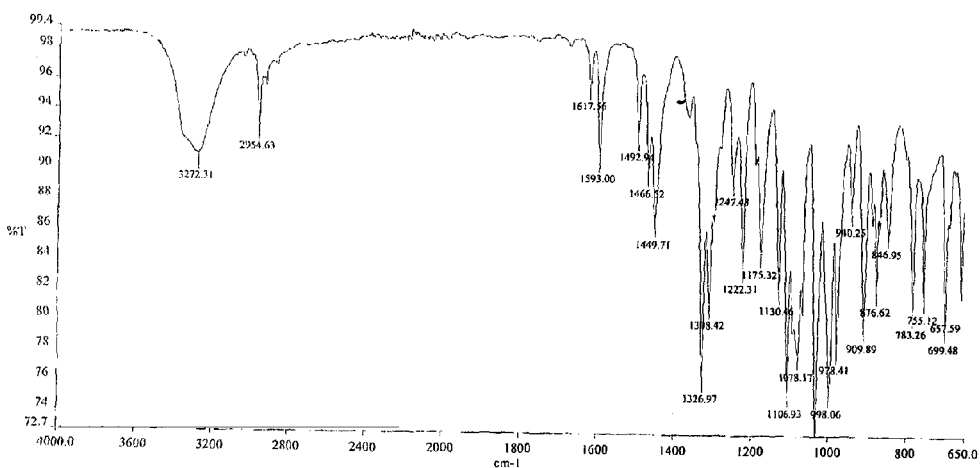
FIG. 5 is the IR spectrum of the Travopost 4. intermediate.

IR spectrum of Travoprost 4. intermediate is shown on FIG. 5.
Travoprost 4. intermediate $^1H$, $^{13}C$ and $^{19}F$ NMR data:

A)

B)

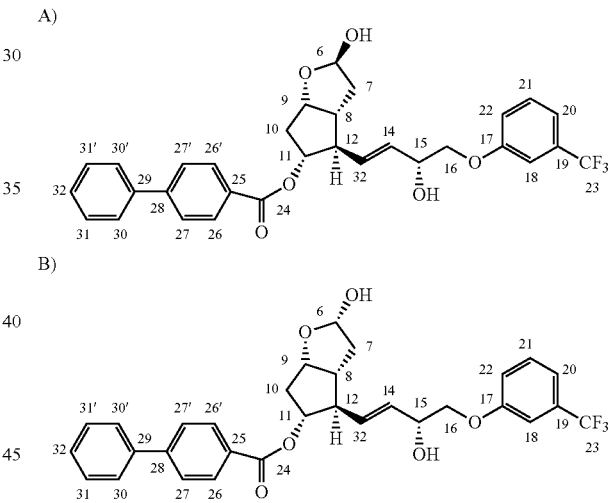

Travoprost 4. intermediate, diastereomer A $^1H$, $^{13}C$ and $^{19}F$ NMR data:

| Numbering | $^{13}C/^{19}F$ (ppm) | $^1H$ (ppm) | Number of $^1H$ | Multiplicity | Coupling constant (Hz) (+/−0.2 Hz) |
|---|---|---|---|---|---|
| 6 | 98.73 | 5.42 | 1 | td | $J_{6,7}$~4.6 and 2.6 |
| 6-OH | | 5.90 | 1 | d | $J_{6,OH}$ = 4.6 |
| 7 | 39.04$ | 1.75 | 2 | m | |
| 8 | 44.65 | 2.27** | 1 | m | |
| 9 | 78.29 | 4.345*** | 1 | td | $J_{8,9} = J_{9,10\beta} = 7.1$; $J_{9,10\alpha} = 4.3$ |
| 10 | 40.58 | β: 2.24** | 1 | m | $J_{gem} = 14.0$; $J_{10\alpha,11} = 9.1$ |
| | | α: 1.44 | 1 | m (ddd) | |
| 11 | 76.60 | 3.67 | 1 | m (dddd) | $J_{10\beta,11} = 7.2$; $J_{11,12} = 9.2$ |
| 11-OH | | 4.80 | 1 | d | $J_{6,OH} = 5.9$ |
| 12 | 55.97 | 1.95+ | 1 | m (td) | $J_{8,12} = 9.2$; $J_{12,13} = 7.4$ |
| 13 | 132.44 | 5.69 | 1 | dd | $J_{13,14} = 15.6$ |
| 14 | 130.30 | 5.55 | 1 | dd | $J_{14,15} = 5.6$ |

| Numbering | $^{13}C/^{19}F$ (ppm) | $^1H$ (ppm) | Number of $^1H$ | Multiplicity | Coupling constant (Hz) (+/−0.2 Hz) |
|---|---|---|---|---|---|
| 15 | 69.24 | 4.32*** | 1 | m | |
| 15-OH | | 5.16++ | 1 | d | $J_{15,OH}$ = 4.9 |
| 16 | 72.48$$ | a: 3.97+++ | 1 | m (dd) | $J_{gem}$ = 9.9; $J_{15,16a}$ = 4.4; |
| | | b: 3.92# | 1 | m (dd) | $J_{15,16b}$ = 7.0 |
| 17 | 158.99$$ | — | — | — | |
| 18 | 111.17 (q) | 7.22 | 1 | m (dd) | $^3J_{C-18,F}$ = 3.7; $J_{18,20}$ = 1.6; $J_{18,22}$ = 3.6 |
| 19 | 130.28 (q) | — | — | — | $^2J_{C-19,F}$ = 31.7 |
| 20 | 117.04 (q) | 7.27## | 1 | m (dd) | $^3J_{C-20,F}$ = 3.8; $J_{20,21}$ = 8.0 |
| 21 | 130.70 | 7.51 | 1 | m (t) | $J_{21,22}$ = 8.0 |
| 22 | 118.93 | 7.25## | 1 | m (dd) | $J_{20,22}$ = 1.0 |
| 23 | 124.03 (q) | — | — | — | $^1J_{C-23,F}$ = 272.5 |
| 23-F | −61.14 (s, 3) | — | — | — | |

*, , *, +, ++, +++, #, ##: Overlapping $^1H$ NMR signals.
$Overlapping $^{13}C$ NMR signals with the signal of DMSO.
$$: Overlapping $^{13}C$ NMR signal.

Travoprost 4. intermediate, diastereomer B H, $^{13}C$ and $^{19}F$ NMR data:

| Numbering | $^{13}C$ (ppm) | $^1H$ (ppm) | Number of $^1H$ | Multiplicity | Coupling constant (Hz) (+/−0.2 Hz) |
|---|---|---|---|---|---|
| 6 | 99.55 | 5.36 | 1 | m (t/ddd) | $J_{6,7\beta}$ = 5.1 |
| 6-OH | | 6.10 | 1 | d | $J_{6,OH}$ = 3.8 |
| 7 | 37.86 | β: 1.92+ | 1 | m | $J_{7,8\beta}$ = 5.7 |
| | | α: 1.61 | 1 | m | $J_{gem}$ = 12.9; $J_{6,7\alpha}$~1.5 |
| 8 | 44.85 | 2.18** | 1 | m (dt/dddd) | $J_{7\alpha,8}$~1.5; $J_{8,12}$ = 9.9 |
| 9 | 80.07 | 4.28*** | 1 | td | $J_{8,9}$ = $J_{9,10\beta}$ = 7.8; $J_{9,10\alpha}$ = 5.7 |
| 10 | 42.88 | β: 2.26** | 1 | m | $J_{gem}$ = 12.7; $J_{10\alpha,11}$ = 9.9 |
| | | α: 1.72* | 1 | m (ddd) | |
| 11 | 76.02 | 3.59 | 1 | m (dddd) | $J_{10\alpha,11}$ = 6.5; $J_{11,12}$ = 9.9 |
| 11-OH | | 4.75 | 1 | d | $J_{6,OH}$ = 5.9 |
| 12 | 55.03 | 2.52### | 1 | m (td) | $J_{12,13}$~7.3, |
| 13 | 133.10 | | | | |
| 14 | 130.08 | | | | |
| 15 | 69.32 | | | | |
| 15-OH | | 5.15++ | 1 | m (d) | $J_{15,OH}$ = 4.9 |
| 16 | 72.53$$ | a: 3.98# | 1 | m (dd) | $J_{gem}$ = 9.9; $J_{15,16a}$ = 4.4 |
| | | b: 3.92# | 1 | m (dd) | $J_{15,16b}$ = 6.9 |
| 17 | 159.01$$ | — | — | — | |

*, ***, +++, #, ##: Overlapping $^1H$ NMR signals.
Overlapping $^1H$ NMR signals with the signal of DMSO.
$$Overlapping $^{13}C$ NMR signals.

5. Construction of the Upper Chain (Preparation of Travoprost Acid)

Preparation of 5-heptanoic acid, 7-[(1R,2R,3R,5S)-3,5-dihydroxy-2-[(1E,3R)-3-hydroxy-4-[3-(trifluoromethyl)phenoxy]-1-buten-1-yl]cyclopentyl]-, (5Z)-
/Compound of formula (VI)/

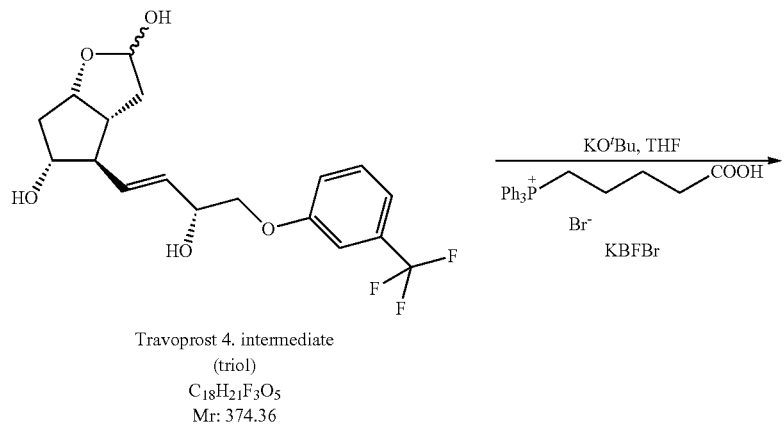

Travoprost 4. intermediate
(triol)
$C_{18}H_{21}F_3O_5$
Mr: 374.36

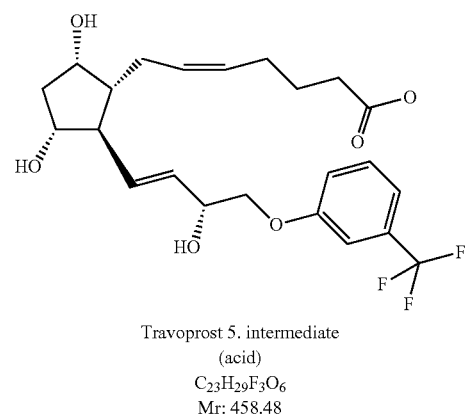

Travoprost 5. intermediate
(acid)
$C_{23}H_{29}F_3O_6$
Mr: 458.48

Under nitrogen atmosphere 1509 g of 4-carboxybutyl-phosphonium bromide (KBFBr) is dissolved in 12.8 L of THF, the solution is cooled to 0° C., and by maintaining that temperature, 1.12 kg of potassium tert-butylate is added to it in portions. After 15 minutes of stirring the reaction mixture is cooled to (−)10° C., then 367 g of triol dissolved in 2.24 L of THF is added and the mixture is stirred at (−10)° C. When the reaction has completed, the reaction mixture is decomposed with water and toluene is added. The aqueous phase is extracted with dichloromethane (DKM) and acidified with a solution of $NaHSO_4$. Ethyl acetate is then added, the phases are separated and the aqueous phase is extracted with ethyl acetate. The united organic phase is washed with a diluted sodium chloride solution, dried over $Na_2SO_4$, the drying material is filtered off, the filtrate is washed and the filtrate solution is evaporated. The residue is crystallized from acetone:diisopropyl ether mixture. The crystals are filtered off, washed with diisopropyl ether:acetone mixture. The mother liquor is evaporated.

Yield: 463 g, 103%

Figure 6:
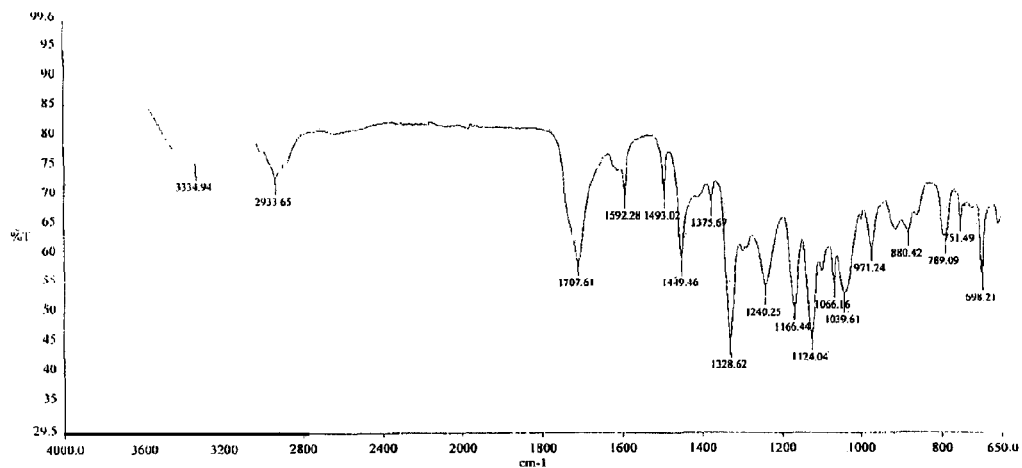
FIG. 6 is the IR spectrum of the Travopost 5. intermediate.

IR spectrum of Travoprost 5. intermediate is shown on FIG. 6.

Travoprost 5. intermediate $^1$H, $^{13}$C and $^{19}$F NMR data:

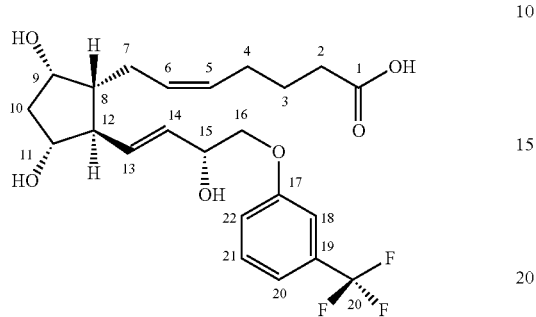

| Numbering | $^{13}$C/$^{19}$F (ppm) | $^1$H (ppm) | Number of $^1$H | Multiplicity | Coupling constant (Hz) (+/− 0.2 Hz) |
|---|---|---|---|---|---|
| 1 | 174.37 | — | — | — | |
| 1-COOH | | 11.95 | 1 | broad (s) | |
| 2 | 33.09 | 2.13* | 2 | t | $J_{2,3} = 7.4$ |
| 3 | 24.46 | 1.49** | 2 | m (tt) | $J_{3,4} = 7.4$ |
| 4 | 26.06 | 1.96*** | 2 | m | |
| 5 | 128.56 | 5.23 | 1 | dt | $J_{5,6} = 10.7; J_{4,5} = 7.2$ |
| 6 | 129.73 | 5.43 | 1 | dt | $J_{6,7} = 7.4$ |
| 7 | 24.78 | b: 2.10* | 1 | m | |
| | | a: 1.96*** | 1 | m | |
| 8 | 48.78 | 1.32 | 1 | m (dddd/tt) | 11.1; 10.0; 5.0; 5.0 |
| 9 | 69.58 | 3.90$^+$ | 1 | m | |
| 9-OH | | 4.36$^{++}$ | 1 | broad (s) | |
| 10 | 43.96 | b: 2.20* | 1 | ddd | $J_{gem} = 14.1; J_{10b,11} = 8.4;$ |
| | | a: 1.44** | 1 | ddd | $J_{9,10b} = 5.8;$ |
| | | | | | $J_{10a,11} = 5.6; J_{9,10a} = 2.3;$ |
| 11 | 75.64 | 3.69 | 1 | m | |
| 11-OH | | 4.53 | 1 | broad (s) | |
| 12 | 54.30 | 2.18* | 1 | m (td) | |
| 13 | 133.97 | 5.57 | 1 | dd | $J_{13,14} = 15.5; J_{12,13} = 8.0$ |
| 14 | 131.01 | 5.51 | 1 | dd | $J_{14,15} = 5.7$ |
| 15 | 69.51 | 4.32$^{++}$ | 1 | q (ddd) | 5.6 |
| 15-OH | | 5.125 | 1 | broad (s) | |
| 16 | 72.55 | b: 3.96$^+$ | 1 | dd | $J_{gem} = 9.9; J_{15,16b} = 4.9$ |
| | | a: 3.93$^+$ | 1 | dd | $J_{15,16a} = 6.6$ |
| 17 | 158.97 | — | — | | |
| 18 | 111.13 (q) | 7.20$^+$ | 1 | m (t/dd) | $^3J_{C-18,F} = 3.7;$ |
| | | | | | $J_{18,20} = 15; J_{18,22} = 2.5$ |
| 19 | 130.29 (q) | — | | | $^2J_{C-19,F} = 31.7$ |
| 20 | 117.01 (q) | 7.26$^{+++}$ | 1 | m (ddd) | $^3J_{C-20,F} = 3.8;$ |
| | | | | | $J_{20,21} = 7.8; J_{20,22} = 0.7$ |
| 21 | 130.68 | 7.50 | 1 | t (dd) | $J_{21,22} = 8.2$ |
| 22 | 118.75 | 7.24$^{+++}$ | 1 | m (ddd) | |
| 23 | 124.01 (q) | — | — | — | $^1J_{C-23,F} = 272.4$ |
| 23-F | −61.19 (s, 3) | — | — | — | |

*, , *, $^+$, $^{++}$, $^{+++}$: Overlapping $^1$H NMR signals.

6. Preparation of Travoprost /Compound of formula (I)/

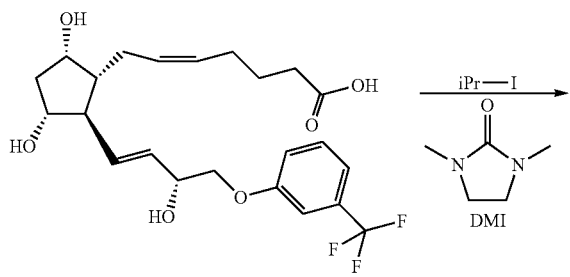

Travoprost 5. intermediate
(acid)
$C_{23}H_{29}F_3O_6$
Mr: 458,48

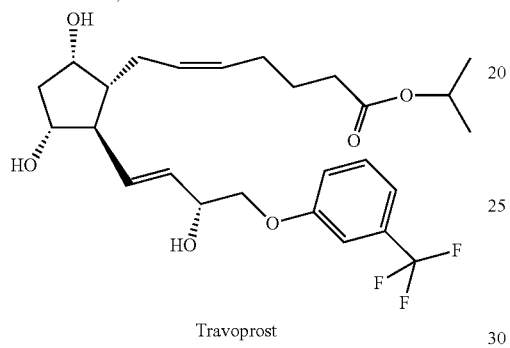

Travoprost
$C_{26}H_{35}F_3O_6$
Mr: 500,56

463 g of Travoprost acid is dissolved in 2.3 L of 1,3-dimethylimidazolidinone (DMI), and 420 g of $K_2CO_3$ and 300 ml of isopropyl iodide are added. The reaction mixture is stirred at 45° C. After the completion of the reaction $NaHSO_4$ solution, water, hexane and ethyl acetate are added. The mixture is shaken, then the phases are separated and the lower, aqueous phase is extracted with hexane:ethyl acetate mixture. The united organic phase is washed with water, dried over $Na_2SO_4$, the drying material is filtered off and the solution is evaporated. The product is purified by chromatography on silica gel, using diisopropyl ether, acetone, dichloromethane, isopropanol mixture as eluent.

Yield: 338.7 g, 67%

Figure 7:
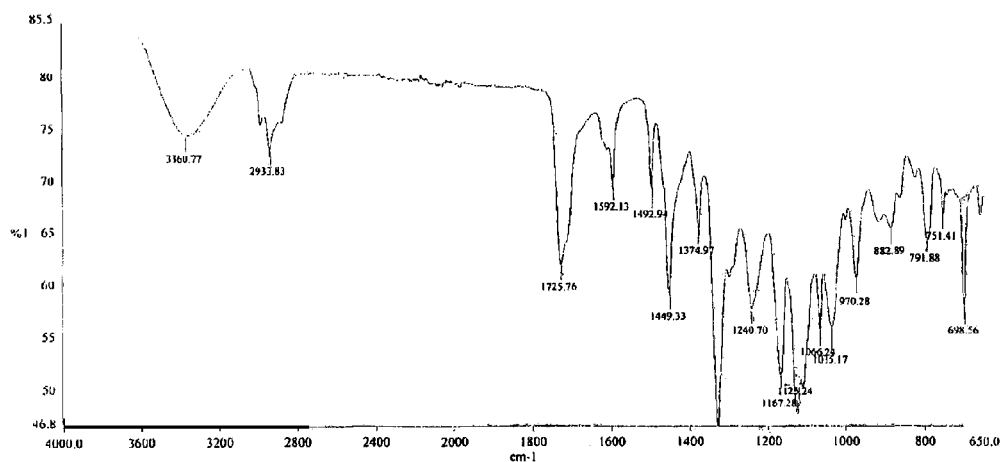
FIG. 7 is the IR spectrum of Travopost.

IR spectrum of Travoprost is shown on FIG. 7.

Travoprost $^1H$, $^{13}C$ and $^{19}F$ NMR data:

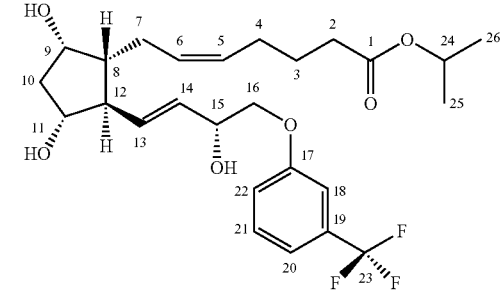

| Numbering | $^{13}C$ (ppm) | $^1H$ (ppm) | Number of $^1H$ | Multiplicity | Coupling constant (Hz) (+/− 0.2 Hz) |
|---|---|---|---|---|---|
| 1 | 172.23 | — | — | — | |
| 2 | 33.19 | 2.16* | 2 | t | $J_{2,3}$ = 7.3 |
| 3 | 24.42 | 1.49** | 2 | tt | $J_{3,4}$ = 7.3 |
| 4 | 25.93 | 1.96*** | 2 | m (q) | $J_{4,5}$ = 7.3 |
| 5 | 128.36 | 5.23 | 1 | dt | $J_{5,6}$ = 10.7 |
| 6 | 129.85 | 5.44 | 1 | dt | $J_{6,7}$ = 7.4 |
| 7 | 24.75 | b: 2.09 | 1 | m (dt) | |
|   |       | a: 1.96*** | 1 | m | |
| 8 | 48.76 | 1.31 | 1 | m (dddd/tt) | 11.2; 10.0; 4.8; 4.8 |
| 9 | 69.54$ | 3.90 | 1 | m (dddd) | 2.0; 5.3; 5.3, 5.3 |
| 9-OH |  | 4.36 | 1 | d | $J_{9,OH}$ = 4.9 |
|   |       | b: 2.20* | 1 | m (ddd) | $J_{gem}$ = 14.1; $J_{10b,11}$ = 8.7; |
| 10 | 43.96 | a: 1.44** | 1 | ddd | $J_{9,10b}$ = 5.9; |
|   |       |            |   |     | $J_{10a,11}$ = 5.7; $J_{9,10a}$ = 2.3; |
| 11 | 75.63 | 3.69 | 1 | m (dddd/tt) | 7.9; 7.9; 5.9; 5.9 |
| 11-OH |  | 4.54 | 1 | d | $J_{11,OH}$ = 5.8 |
| 12 | 54.30 | 2.175* | 1 | m | |
| 13 | 134.01 | 5.57 | 1 | dd | $J_{13,14}$ = 15.5; $J_{12,13}$ = 8.0 |
| 14 | 131.03 | 5.51 | 1 | dd | $J_{14,15}$ = 6.0 |
| 15 | 69.54$ | 4.315 | 1 | qui (tt) | 5.5 |
| 15-OH |  | 5.12 | 1 | d | $J_{15,OH}$ = 4.8 |
|   |       | a: 3.94 | 1 | m | |
| 16 | 72.55 | b: 3.95 | 1 | m | |
| 17 | 158.96 | — | — | — | |
| 18 | 111.07 (q) | 7.20 | 1 | m | $^3J_{C-18,F}$ = 3.7; |
|   |       |      |   |   | $J_{18,20}$ = ; $J_{18,22}$ = 2.0 |
| 19 | 130.28 (q) | — | — | — | $^2J_{C-19,F}$ = 31.8 |
| 20 | 117.02 (q) | 7.27+ | 1 | t | $^3J_{C-20,F}$ = 3.9; |
|   |       |      |   |   | $J_{20,21}$ = 8.0; $J_{20,22}$ = 0.7 |
| 21 | 130.67 | 7.51 | 1 | t | $J_{21,22}$ = 8.0; |
| 22 | 118.77 | 7.24+ | 1 | dd | |
| 23 | 124.01 (q) | — | — | — | $^1J_{C-23,F}$ = 272.2 |
| 23-F | −61.28 (s, 3) | — | — | — | |

-continued

| Numbering | $^{13}$C (ppm) | $^1$H (ppm) | Number of $^1$H | Multiplicity | Coupling constant (Hz) (+/- 0.2 Hz) |
|---|---|---|---|---|---|
| 24 | 66.80 | 4.84 | 1 | sep | $J_{24,25} = 6.3$ |
| 25; 26 | 21.55 | 1.13 | 6 | d | |

$: Overlapping $^{13}$C NMR signals.
*, , *, †: Overlapping $^1$H NMR signals.

The invention claimed is:
1. A process for the preparation of travoprost of formula (I):

(I)

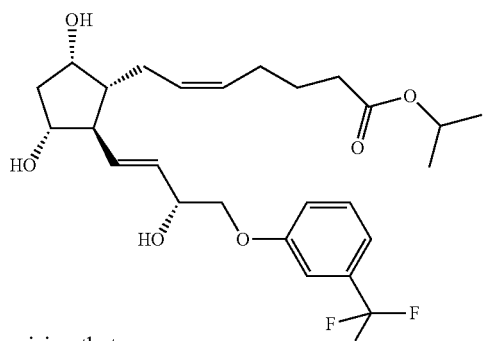

comprising that,
the compound of formula (II):

(II)

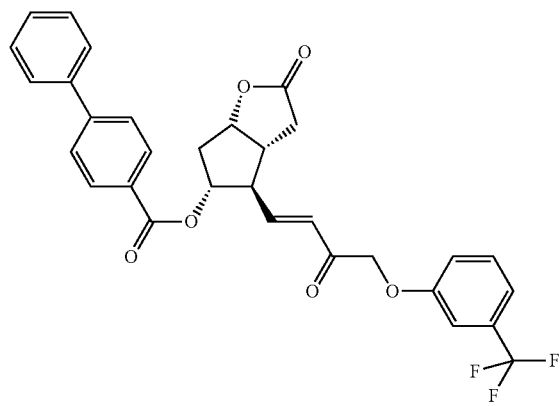

is stereoselectively reduced, the borane-type reducing agent, which is catcholborane, in the presence of chiral catalyst, which is CBS-oxazaborolidine, the resulting compound of formula (III)

(III)

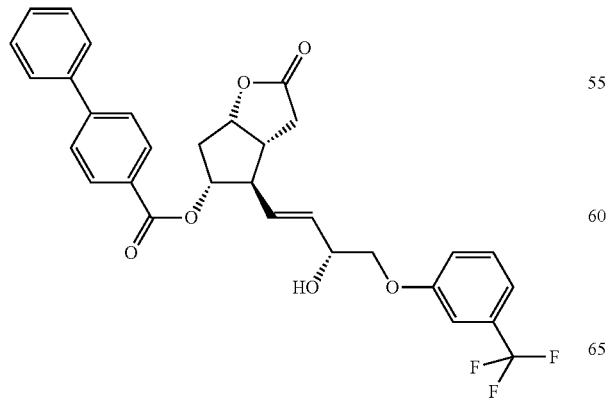

is if desired crystallized, the lactone group of the compound of formula (III) is reduced by diisobutylaluminium hydride, the p-phenyl-benzoyl protecting group of the thus obtained compound of formula (IV)

(IV)

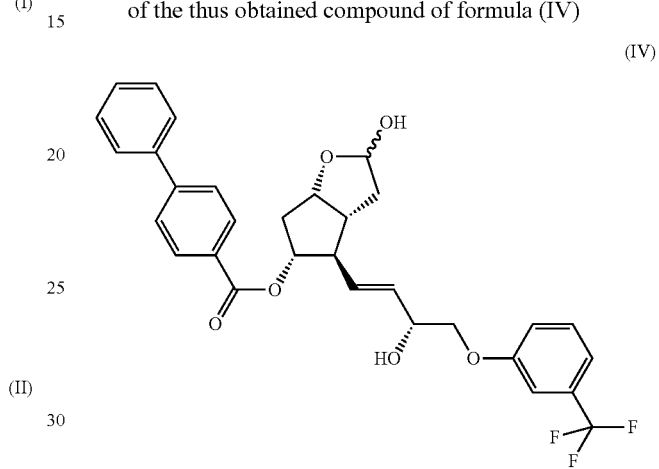

is removed by methanolysis, the resulting triol of formula (V)

(V)

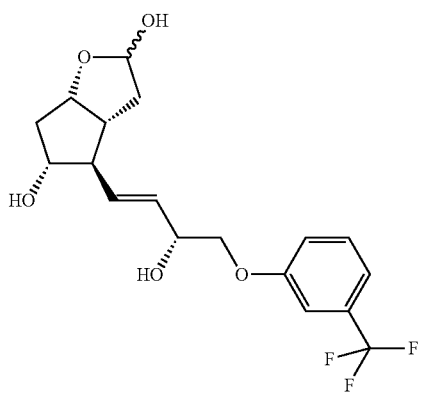

is if desired after crystallization transformed by Wittig reaction using 4-carboxybutyl-phosphonium bromide into the acid of formula (VI), (VI)

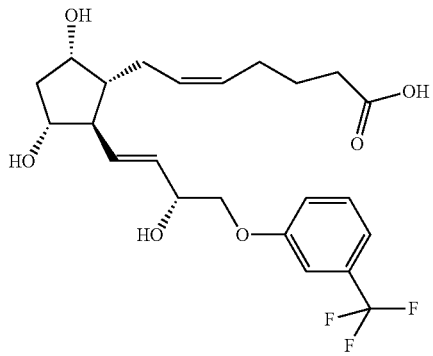

which is then esterified in a cyclic tertiary-amide type solvent by isopropyl iodide.

2. The process as defined in claim 1, comprising that the reduction by borane-type reducing agent is performed in hydrocarbon- or ether-type solvents.

3. The process as defined in claim 2, comprising that the reduction by borane-type reducing agent is performed in toluene, hexane, pentane, tetrahydrofuran, methyltetrahydrofuran, cyclopentyl methyl ether, dimethoxyethane, tert-butyl methyl ether, diisopropyl ether, diethyl ether or in the mixture of them.

4. The process as defined in claim 3, comprising that the reduction by borane-type reducing agent is performed in a toluene-tetrahydrofuran mixture.

5. The process as defined in claim 1, comprising that the reduction by borane-type reducing agent is carried out at a temperature between −10 and −90° C.

6. The process as defined in claim 5, comprising that the reduction by borane-type reducing agent is carried out at a temperature between −10 and −20° C.

7. The process as defined in 1, comprising that the resulting compound of formula (III) is purified by crystallization.

8. The process as defined in claim 7, comprising that the crystallization is carried out in hydrocarbon, chlorinated hydrocarbon, ether, ester, ketone or alcohol-type solvents or in the mixture of them.

9. The process as defined in claim 8, comprising that the crystallization is carried out repeatedly, in different solvents or in the mixture of them.

10. The process as defined in claim 9, comprising that the crystallization is carried out in (i) a hexane:acetone mixture, (ii) methanol, or (iii) a hexane:acetone mixture and methanol.

11. The process as defined in claim 7, further comprising:
dissolving the resulting compound of formula (III) in alcohol at a reflux temperature between −20 and 70° C.,
crystallizing the resulting compound of formula (III) by cooling gradually, filtering off, washing, and drying the resulting compound of formula (III).

12. The process as defined in claim 1, comprising that the p-phenylbenzoyl protecting group of the compound of formula (IV) is removed by methanolysis, under basic conditions.

13. The process as defined in claim 12, comprising that the protecting group is removed in the presence of potassium carbonate.

14. The process as defined in claim 1, comprising that the intermediate of formula (V) is purified by crystallization.

15. The process as defined in claim 14, comprising that the crystallization is carried out in the mixture of polar and apolar solvents.

16. The process as defined in claim 15, comprising that the crystallization is carried out in ethyl acetate-hexane mixture.

17. The process as defined in claim 15, wherein crystallization is repeated until an amount of undesired isomer is less than 0.05%.

18. The process as defined in claim 1, comprising that as cyclic tertiary-amide type solvent N-methylpyrrolidone or 1,3-dimethylimidazolidinone is applied.

19. The process as defined in claim 1, comprising that the esterification is carried out within a temperature range of 20 to 90° C.

20. The process as defined in claim 19, comprising that the esterification is carried out within a temperature range of 40 to 50° C.

21. The process as defined in claim 1, comprising that the product of formula (I) is purified by chromatography.

22. The process as defined in claim 21, comprising that the product is purified by gravimetric silica gel chromatography.

23. The process as defined in claim 22, comprising that the chromatographic purification is performed using hydrocarbon, chlorinated hydrocarbon, ether, ester, alcohol, ketone and acid-type solvents or their mixtures, as eluents.

24. The process as defined in claim 1, wherein the CBS-oxazaborolidine chiral catalyst is R-(+)-2-methyl-CBS-oxaborolidine.

\* \* \* \* \*